(12) United States Patent
Yazaki et al.

(10) Patent No.: US 7,713,997 B2
(45) Date of Patent: May 11, 2010

(54) PYRIDONECARBOXYLIC ACID DERIVATIVES OR SALTS THEREOF

(75) Inventors: Akira Yazaki, Akitakata (JP); Yasuhiro Kuramoto, Akitakata (JP); Kenji Itoh, Akitakata (JP); Kazusa Yoshikai, Akitakata (JP); Yuzo Hirao, Akitakata (JP); Yoshihiro Ohshita, Akitakata (JP); Norihiro Hayashi, Akitakata (JP); Hirotaka Amano, Akitakata (JP); Takayuki Amago, Akitakata (JP); Hitomi Takenaka, Akitakata (JP)

(73) Assignee: Wakunaga Pharmaceutical Co., Ltd., Osaka-shi (JP)

( * ) Notice: Subject to any disclaimer, the term of this patent is extended or adjusted under 35 U.S.C. 154(b) by 390 days.

(21) Appl. No.: 11/719,547

(22) PCT Filed: Nov. 17, 2005

(86) PCT No.: PCT/JP2005/021093

§ 371 (c)(1),
(2), (4) Date: May 17, 2007

(87) PCT Pub. No.: WO2006/054623

PCT Pub. Date: May 26, 2006

(65) Prior Publication Data

US 2009/0149440 A1    Jun. 11, 2009

(30) Foreign Application Priority Data

Nov. 17, 2004    (JP)    ............... 2004-333244

(51) Int. Cl.
C07D 215/38    (2006.01)
A61K 38/02    (2006.01)

(52) U.S. Cl. .................. 514/312; 546/156
(58) Field of Classification Search .......... 514/312, 514/314; 546/153, 159, 156
See application file for complete search history.

(56) References Cited

U.S. PATENT DOCUMENTS 5,998,436 A * 12/1999 Yazaki et al. ............ 514/312
6,133,284 A * 10/2000 Yazaki et al. ............ 514/312
6,156,903 A * 12/2000 Yazaki et al. ............ 546/307

FOREIGN PATENT DOCUMENTS

| WO | 97 11068 | 3/1997 |
| WO | 01 02390 | 1/2001 |
| WO | 02 058695 | 8/2002 |

* cited by examiner

*Primary Examiner*—D. Margaret Seaman
(74) *Attorney, Agent, or Firm*—Oblon, Spivak, McClelland, Maier & Neustadt, L.L.P.

(57) ABSTRACT

The present invention provides an agent which exhibits excellent antibacterial activity, low toxicity, improved bioavailability, and low binding rate to serum proteins. The present invention is directed to a pyridonecarboxylic acid derivative represented by formula (1):

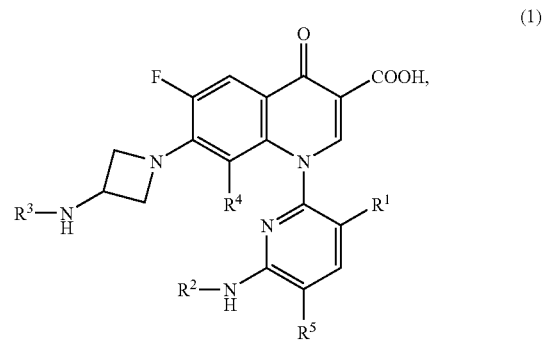

or a salt thereof, wherein $R^1$ represents a methyl group, a fluorine atom, or a chlorine atom; $R^2$ represents a hydrogen atom or a lower alkyl group; $R^3$ represents an isopropyl group or a tert-butyl group; $R^4$ represents a methyl group or a halogen atom; and $R^5$ represents a fluorine atom or a chlorine atom. The present invention is also directed to an antibacterial agent and a medicament containing the derivative or the salt thereof as an active ingredient.

16 Claims, No Drawings

PYRIDONECARBOXYLIC ACID DERIVATIVES OR SALTS THEREOF

TECHNICAL FIELD

The present invention relates to a pyridonecarboxylic acid derivative or a salt thereof, which exhibits excellent antibacterial activity and high bioavailability.

BACKGROUND ART

Among compounds having a pyridonecarboxylic acid as base skeleton, there have been known many compounds, which are useful synthetic antibacterial agents, by virtue of their excellent antibacterial activity and broad antibacterial spectrum. Among such compounds, compounds such as norfloxacin (see Patent Document 1), enoxacin (see Patent Document 2), ofloxacin (see Patent Document 3), ciprofloxacin (see Patent Document 4), and tosufloxacin (Patent Document 5) are extensively used in clinical application as therapeutic agents for infectious diseases. However, these compounds are still unsatisfactory in terms of, for example, antibacterial activity, intestinal absorption, metabolic stability, and side effects; particularly phototoxicity and cytotoxicity.

The present inventors previously conducted extensive studies in order to solve the aforementioned problems, and found that, pyridonecarboxylic acid derivatives having a substituted pyridyl group at the 1-position of the pyridonecarboxylic acid moiety, especially those having an aminoazetidinyl group at the 7-position of the pyridonecarboxylic acid moiety, have remarkably excellent characteristics; i.e. exhibit remarkably potent antibacterial activity, and, unlike most of pyridonecarboxylic acid class of synthetic antibacterial agents, do not produce phototoxicity (Patent Documents 6 and 7).

Another requirement for drugs to perform their abilities efficiently on the treatment of infectious diseases is high bioavailability of the drugs, more preferably, a higher blood level of the free form of drugs. This latter property is closely related to binding of the drug to serum proteins. That is, the drug with lower binding rate to serum proteins results in higher proportion of free form of the drug in the blood. Therefore, a drug exhibiting higher bioavailability and lower binding rate to serum proteins is a more preferred therapeutic agent for infectious diseases.

The pyridonecarboxylic acid derivative having a substituted pyridyl group at the 1-position and an aminoazetidinyl group at the 7-position is improved its bioavailability by introducing an alkyl group to the amino group on the azetidine ring and increasing the number of carbon atoms of the alkyl group so as to enhance lipophilicity of the derivative. However such modification is also prone to enhance the binding rate of the derivative to serum proteins.

Patent Document 1: Japanese Patent Application Laid-Open (kokai) No. 53-141286

Patent Document 2: Japanese Patent Application Laid-Open (kokai) No. 55-031042

Patent Document 3: Japanese Patent Application Laid-Open (kokai No. 57-046986

Patent Document 4: Japanese Patent Application Laid-Open (kokai) No. 58-076667

Patent Document 5: Japanese Patent Application Laid-Open (kokai) No. 60-228479

Patent Document 6: WO 97/11068 Pamphlet

Patent Document 7: WO 01/02390 Pamphlet

DISCLOSURE OF THE INVENTION

Problems to be Solved by the Invention

An object of the present invention is to provide an agent with excellent antibacterial activity, low toxicity, improved bioavailability, and low binding rate to serum proteins.

Means for Solving the Problems

For the purpose of solving the problems, the present inventors have extremely evaluated the aforementioned pyridonecarboxylic acid derivatives having a substituted pyridyl group at the 1-position and an aminoazetidinyl group at the 7-position, and found that, even in the case that an alkyl group is introduced to the amino group of the azetidine ring so as to increase lipophilicity, a compound represented by the following formula (1) having an isopropyl group or a tert-butyl group introduced to the amino group is possible to have improved bioavailability without elevating its binding rate to serum proteins. The inventors have also found that a compound represented by the following formula (2) is useful intermediates for the synthesis of the compound represented by formula (1).

Accordingly the present invention is directed to a pyridonecarboxylic acid derivative represented by formula (1):

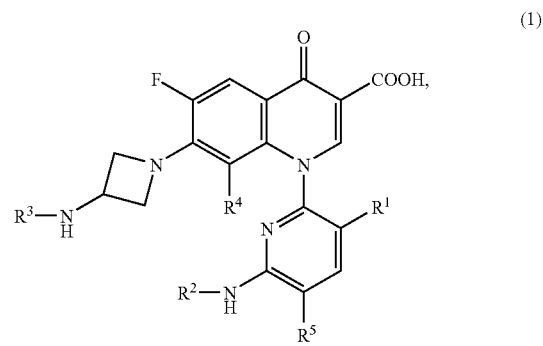

(1)

or a salt thereof, wherein $R^1$ represents a methyl group a fluorine atom, or a chlorine atom; $R^2$ represents a hydrogen atom or a lower alkyl group; $R^3$ represents an isopropyl group or a tert-butyl group; $R^4$ represents a methyl group or a halogen atom; and $R^5$ represents a fluorine atom or a chlorine atom.

The present invention is also directed to 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid or a salt thereof.

The present invention is also directed to a medicament comprising the pyridonecarboxylic acid derivative or the salt thereof as an active ingredient.

The present invention is also directed to an antibacterial agent comprising the pyridonecarboxylic acid derivative or the salt thereof as an active ingredient.

The present invention is also directed to a pharmaceutical composition comprising the pyridonecarboxylic acid derivative or the salt thereof, and a pharmaceutically acceptable carrier.

The present invention is also directed to use of the pyridonecarboxylic acid derivative or the salt thereof, for manufacturing a medicament.

The present invention is also directed to a method for treating an infectious disease, comprising administering the pyridonecarboxylic acid derivative or a salt thereof.

The present invention is also directed to a pyridonecarboxylic acid derivative represented by formula (2):

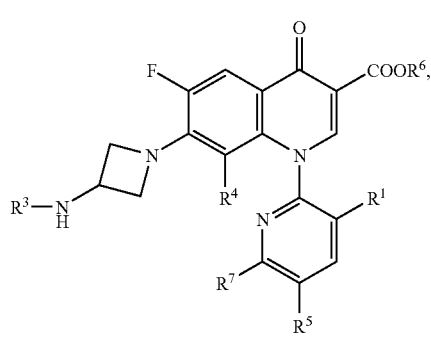

(2)

or a salt thereof, wherein $R^1$ represents a methyl group, a fluorine atom, or a chlorine atom; $R^3$ represents an isopropyl group or a tert-butyl group; $R^4$ represents a methyl group or a halogen atom; $R^5$ represents a fluorine atom or a chlorine atom; $R^6$ represents a hydrogen atom or a carboxyl protective group; and $R^7$ represents —$NR^2R^8$, wherein $R^2$ represents a hydrogen atom or a lower alkyl group, and $R^8$ represents a hydrogen atom or an amino protective group, with the proviso that $R^6$ and $R^8$ do not simultaneously represent hydrogen atoms.

Effects of the Invention

According to the present Invention, an antibacterial agent with remarkably excellent antibacterial activity, no phototoxicity, high bioavailability, and low binding rate to serum proteins can be provided.

BEST MODES FOR CARRYING OUT THE INVENTION

The pyridonecarboxylic acid derivative of the present invention represented by formula (1) or the salt thereof is useful as an antibacterial agent, and the pyridonecarboxylic acid derivative represented by formula (2) or the salt thereof is useful as an intermediate for manufacturing the pyridonecarboxylic acid derivative represented by formula (1).

Examples of the lower alkyl group ($R^2$) in formula (1) or (2) include linear or branched C1 to C6 alkyl groups such as methyl, ethyl, propyl, isopropyl, butyl, isobutyl, tert-butyl, pentyl, and hexyl. Of these, linear or branched C1 to C3 alkyl groups such as methyl, ethyl, propyl, and isopropyl are preferred, with methyl being particularly preferred.

Examples of the halogen atom ($R^4$) include fluorine, chlorine, bromine, and iodine, with chlorine and bromine being particularly preferred.

The carboxyl protective group ($R^6$) refers to an ester residue of a carboxylic acid ester, and includes those relatively readily cleaved to generate a corresponding free carboxyl group. Examples of the protective group include groups leaving through treatment under mild conditions (e.g., hydrolysis and catalytic reduction), such as C1 to C6 lower alkyl groups (e.g., methyl, ethyl, propyl, isopropyl, butyl, isobutyl, tert-butyl, pentyl, and hexyl); C1 to C8 alkenyl groups (e.g., vinyl, allyl, 1-propenyl, butenyl, pentenyl, hexenyl, and heptenyl); C7 to C11 aralky groups (e.g., benzyl); and C6 to C14 aryl groups (e.g., phenyl and naphthyl), and groups readily leaving in vivo, such as lower alkanoyloxy-lower alkyl groups (e.g., acetoxymethyl and pivaloyloxymethyl); lower alkoxycarbonyloxy-lower alkyl group (e.g., methoxycarbonyloxymethyl and 1-ethoxycarbonyloxyethyl); lower alkoxy-lower alkyl groups (e.g., methoxymethyl); lactonyl groups (e.g., phthalydyl); di-lower alkylamino-lower alkyl groups (e.g., 1-dimethylaminoethyl); and (5-methyl-2-oxo-1,3-dioxol-4-yl)methyl.

Examples of the amino protective group ($R^8$) include groups readily leaving by hydrolysis or catalytic reduction, such as benzyl, 1-phenylethyl, tert-butoxycarbonyl, benzyloxycarbonyl and benzhydryl.

Among the pyridonecarboxylic acid derivatives represented by formula (1) compounds in which $R^1$ is a fluorine atom, $R^2$ is a hydrogen atom or a methyl group, $R^4$ is a bromine atom or a methyl group, and $R^5$ is a fluorine atom are preferred from the viewpoint of the effects of the present invention, wherein those in which $R^3$ is an isopropyl group are particularly preferred.

The pyridonecarboxylic acid derivative represented by formula (1) or (2) may form an acid addition salt with an acid or a base addition salt with a base. Examples of the acid addition salt may include: (a) salts with a mineral acid such as hydrochloric acid and sulfuric acid; (b) salts with an organic carboxylic acid such as formic acid, acetic acid, citric acid, trichloroacetic acid, trifluoroacetic acid, fumaric acid, and maleic acid; and (c) salts with a sulfonic acid such as methanesulfonic acid, benzenesulfonic acid, p-toluenesulfonic acid, mesitylenesulfonic acid, and naphthalenesulfonic acid. Examples of the base addition salt may include: (a') salts with an alkali metal such as sodium and potassium; (b') salts of an alkaline earth metal such as calcium and magnesium; (c') ammonium salts; and (d') salts with a nitrogen-containing organic base such as trimethylamine, triethylamine, tributylamine, pyridine, N,N-dimethylaniline, N-methyl-D(−)-glucamine, N-methylpiperidine, N-methylmorpholine, diethylamine, cyclohexylamine, procaine, dibenzylamine, N-benzyl-β-phenethylamine, 1-ephenamine, and N,N'-dibenzylethylenediamine. Examples of boron compounds include boron halides such as boron fluoride; and lower acyloxyboron such as acetoxyboron.

The pyridonecarboxylic acid derivative represented by formula (1) or (2) or the salt thereof may be present in the non-solvated form, or as a hydrate or solvate. Thus, the present invention encompasses all crystal forms, hydrates, and solvate of the pyridonecarboxylic acid derivative.

The pyridonecarboxylic acid derivative (1) and the intermediate (2) may be produced by any methods, for example, the following scheme:

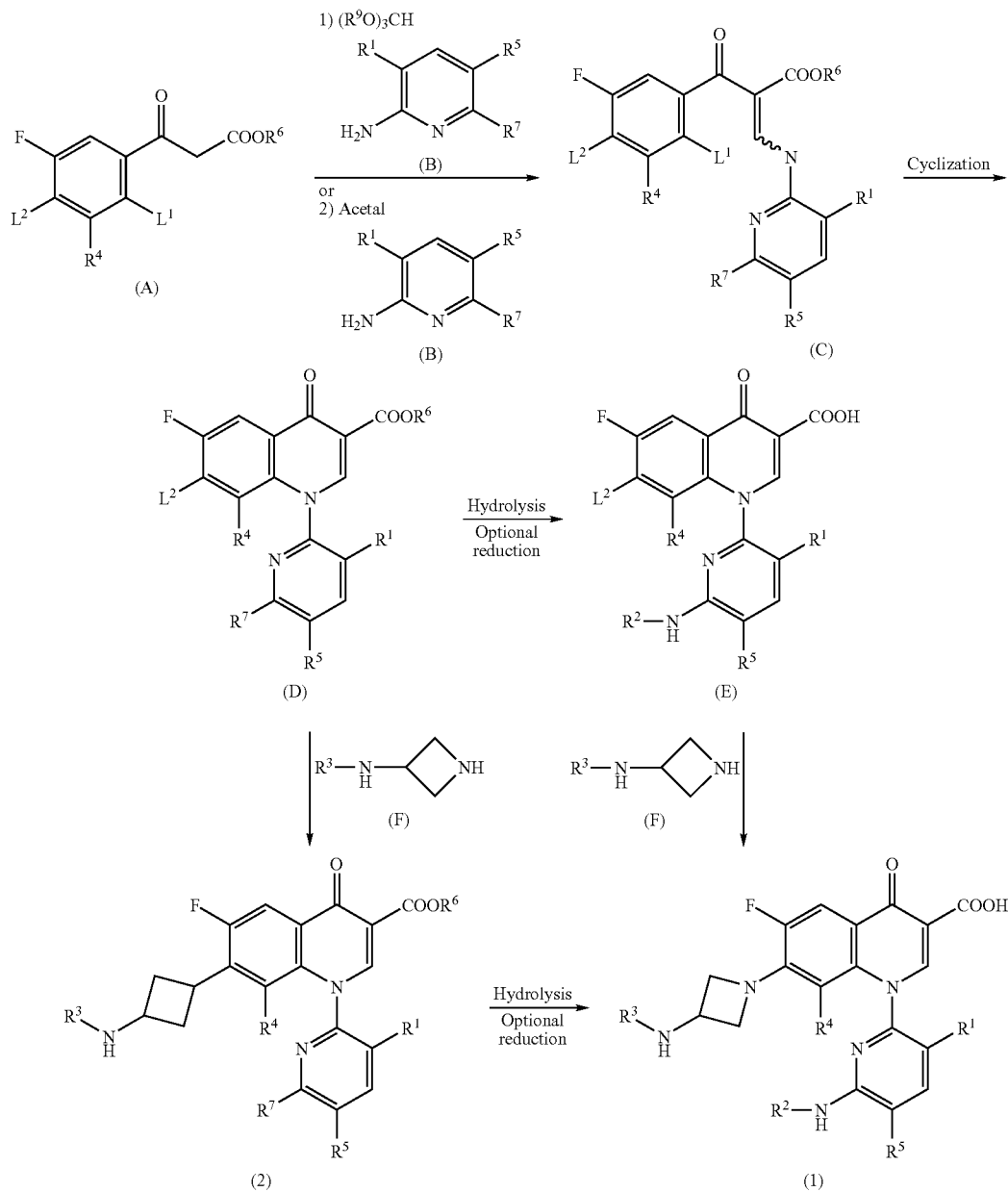

(wherein each of $L^1$ and $L^2$ represents a halogen atom such as fluorine or chlorine; $R^9$ represents a C1 to C5 alkyl group; and $R^1$, $R^2$, $R^3$, $R^4$, $R^5$, $R^6$, and $R^7$ represent the same as defined above).

Specifically, a compound (A) is reacted with an ortho-formic acid ester $(R^9O)_3CH$, and further with an amino compound (B), to form a compound (C). Alternatively, a compound (A) is reacted with an acetal and further with an amino compound (B), to form a compound (C) Subsequently, a compound (c) is cyclized to form a quinoline ring, to yield a compound (D), which is then hydrolized, and optionally further subjected to deprotection reaction such as reduction, to form a compound (E). The compound (E) is aminated with an azetidine derivative (F), to yield a pyridonecarboxylic acid derivative (1).

Alternatively, after amination of the compound (D) with an azetidine derivative (F) to produce a pyridonecarboxylic acid derivative (2), the derivative (2) is hydrolyzed and optionally subjected to deprotection such as reduction, to yield a pyridonecarboxylic acid derivative (1).

Reaction between the compound (A) and the ortho-formic acid ester is generally performed at 0 to 160° C., preferably 50 to 150° C. for 10 minutes to 48 hours, preferably for 1 to 10 hours. The ortho-formic acid ester is preferably used in an equimole amount or more with respect to compound (A), particularly about 1 to 10 times by mol. A carboxylic anhydride such as acetic anhydride is preferably added as an auxiliary agent. The auxiliary agent is preferably used in an equimole amount or more with respect to compound (A), particularly about 1 to 10 times by mole. In the reaction of compound (A) with amino compound (BS in the absence of solvent or in the presence of an appropriate solvent to form a compound (C), the amino compound (B) is preferably used in an equimole amount or more with respect to compound (A), particularly equimole to 2 times by mole. No particular limitation is imposed on the solvent employed in the reaction so long as the solvent does not affect this reaction Examples of the solvent include aromatic hydrocarbons such as benzene, toluene, and xylene; ethers such as diethyl ether tetrahydrofuran, 1,4-dioxiane, monoglyme, and diglyme; aliphatic hydydrocarbons such as pentane, hexane, heptane, and ligroin; halohydrocarbons such as methylene chloride, chloroform, and tetrachlorocarbon; aprotic polar solvents such as N,N-dimethylformamide and dimethyl sulfoxide; and alcohols such as methanol, ethanol, and propanol. The above reaction is generally performed at 0 to 150° C., preferably 0 to 100° C., for 10 minutes to 48 hours.

In another alternative way, the compound (A) may be reacted with an acetal such as N,N-dimethylformamide dimethylacetal and N,N-dimethylformamide diethyl acetal, followed by reacting with an amino compound (B), to form a compound (C). No particular limitation is imposed on the solvent employed in the reaction with acetal, so long as the solvent does not affect the reaction. Specifically, the same solvents as mentioned above may be employed. The reaction is generally carried out at 0 to 150° C. for 10 minutes to 48 hours, preferably room temperature to 100° C., for 1 to 10 hours.

Cyclization of the compound (C) to form a compound (D) is carried out in an appropriate solvent in the presence or absence of a basic compound. No particular limitation is imposed on the solvent employed in the reaction so long as the solvent does not affect the reaction. Examples of the solvent include aromatic hydrocarbons such as benzene, toluene, and xylene; ethers such as diethyl ether, tetrahydrofuran, dioxane, monoglyme, and diglyme; halohydrocarbons such as methylene chloride, chloroform, and tetrachlorocarbon; aprotic polar solvents such as dimethylformamide and dimethyl sulfoxide; alcohols such as methanol, ethanol, and propanol. Examples of the basic compound employed in the reaction include alkali metals such as metallic sodium and metallic potassium; metal hydrides such as sodium hydride and calcium hydride; inorganic salts such as lithium hydroxide, sodium hydroxide, potassium hydroxide, sodium carbonate, and potassium carbonate; alkoxides such as sodium methoxide, sodium ethoxide, and potassium tert-butoxide; metal fluorides such as sodium fluoride and potassium fluoride; and organic bases such as triethylamine and 1,8-diazabicyclo[5.4.0]undecene (DBU). The reaction is generally performed at 0 to 200° C. preferably room temperature to 180° C., and is generally completed within 5 minutes to 24 hours. The basic compound is used in an equimole amount or more with respect to compound (C), preferably equimole to 2 times by mole.

Through hydrolysis of the compound (D) and optional reduction, a compound (E) can be obtained.

The hydrolysis may be performed under any conventional reaction conditions. For example, the hydrolysis is performed in the presence of a basic compound such as sodium hydroxide, potassium hydroxide, sodium carbonate, or potassium carbonate; a mineral acid such as hydrochloric acid, sulfuric acid, or hydrobromic acid; or an organic acid such as p-toluenesulfonic acid, in a solvent such as water; alcohols (e.g., methanol, ethanol, or propanol); ethers (e.g., tetrahydrofuran or dioxane); ketones (e.g., acetone or methyl ethyl ketone); or acetic acid, or a mixture thereof. The reaction is generally performed at room temperature to 180° C., preferably room temperature to 140° C., for 1 to 24 hours.

The reduction may be catalytic reduction performed in the presence of, for example, palladium-carbon or palladium hydroxide-carbon, by use of a hydrogen source such as hydrogen or ammonium formate, in a solvent such as alcohols (e.g., methanol or ethanol) or acetic acid, at room temperature to 100° C., preferably 70 to 120° C., for 30 minutes to 10 hours, preferably 1 to 5 hours.

When the compound (E) is further reacted with an azetidine derivative (F), a pyridonecarboxylic acid derivative (1) of the present invention can be obtained.

The reaction is carried out in a solvent which does not affect the reaction. Examples of the solvent include aromatic hydrocarbons such as benzene toluene, and xylene; alcohols such as methanol or ethanol; ethers such as tetrahydrofuran, dioxane and monoglyme; halohydrocarbons such as methylene chloride, chloroform, and tetrachlorocarbon; aprotic polar solvents such as dimethylformamide, dimethyl sulfoxide, and N-methylpyrrolidone; acetonitrile; and pyridine, optionally in the presence of deoxidizing agents such as sodium carbonate, calcium carbonate, lithium hydroxide, triethylamine, 1,8-diazabicyclo[5.4.0]undecene (DBU), N-methylpyrrolidine, or 1,1,3,3-tetramethylguanidine, and optionally in the presence of additives such as lithium chloride, lithium perchlorate, or lithium trifluoromethanesulfonate, at room temperature to 160° C. The reaction time is several minutes to 48 hours, preferably 10 minutes to 24 hours. The azetidin derivative is used in an equimole amount or more with respect to compound (E), preferably equimole to 5 times by mole.

Production of a pyridonecarboxylic acid derivative (1) of the present invention from a compound (D) via a pyridonecarboxylic acid derivative (2) of the present invention may be performed through the same reactions as mentioned above.

The pyridonecarboxylic acid derivative (1) of the present invention may be transformed to an acid addition salt or a base addition salt by a conventional method. The reaction is performed in a polar solvent such as water or an alcohol (e.g., methanol or ethanol), at room temperature or heating the pyridonecarboxylic acid derivative (1) of the present invention with a mineral acid such as hydrochloric acid or sulfuric acid; an organic carboxylic acid such as formic acid, acetic acid, citric acid, trichloroacetic acid, trifluoroacetic acid, fumaric acid, or maleic acid; a sulfonic acid such as methanesulfonic acid, benzenesulfonic acid, p-toluenesulfonic acid, mesitylenesulfonic acid, or naphthalenesulfonic acid, or with a basic compound such as sodium hydroxide, potassium hydroxide, calcium hydroxide, or magnesium hydroxide; ammonia; or a nitrogen-containing organic base such as trimethylamine, triethylamine, tributylamine, pyridine, N,N-dmethylaniline, N-methylpiperidine, N-methylmorpholnie, diethylamine, cyclohexylamine, procaine, dibenzylamine, N-benzyl-β-phenethylamine, 1-ephenamine, N,N'-dibenzylethylenediamine or N-methyl-D-glucamine.

A starting compound (A) may be produced through, for example, methods disclosed in the following literature or similar methods.

(1) J. Heterocyclic Chem 22, 1033 (1985)
(2) Liebigs Ann. Chem. 29 (1987)
(3) J. Med. Chem. 31, 991 (1988)
(4) J. Org. Chem. 35, 930 (1970)
(5) Japanese Patent Application Laid-open (kokai) No. 62-246541
(6) Japanese Patent Application Laid-Open (kokai) No. 62-26272
(7) Japanese Patent Application Laid-Open (kokai) No. 63-145268
(8) J. Med. Chem. 29, 2363 (1986)

(9) J. Fluorin Chem. 28, 361 (1985)
(10) Japanese Patent Application Laid-Open (kokai) No. 63
(11) Japanese Patent Application Laid-open (kokai) No. 63-264461
(12) Japanese Patent Application Laid-Open (kokai) No. 63-104974

A starting compound (B) may be produced through any methods, for example, the reaction disclosed in Japanese Patent Application Laid-Open (kokai) No. 11-322715.

The compounds produced in the above steps may be isolated and purified though conventional methods. Depending on the isolation and purification conditions, the products may be provided as a salt form, a free carboxylic acid form, or a free amine form. These forms may be optionally interconverted, whereby a compound of the present invention of a desired form can be produced.

As shown in the Test Examples 1 to 4 hereinbelow, the pyridonecarboxylic acid derivative (1) or a salt thereof having a substituted pyridyl group at the 1-position and an isopropylaminoazetidinyl group or a tert-butylaminoazetidinyl group at the 7-position, obtained in the above procedure, not only exhibits excellent antibacterial activity and no phototoxicity (a characteristic toxicity of quinolone compounds) as the compounds disclosed in WO 97/11068 and WO 01/02390 (i.e., Comparative compounds 1 to 4), but also exhibits higher bioavailability and lower binding rate to serum proteins compared to the Comparative compounds. Thus, the pyridonecarboxylic acid derivative (1) of the present invention or a salt thereof fully attains their intrinsic excellent antibacterial activity in vivo. Note that the term "serum protein" refers to albumin (HAS), acidic glucoprotein (AGP), and lipoprotein (AFP) in blood, and the term "binding rate to serum proteins" means the ratio of the amount of a compound bound to serum proteins in a blood sample to the total amount of the compound in the blood sample.

Therefore, the pyridonecarboxylic acid derivative (1) of the present invention or a salt thereof is generally useful as antibacterial agents; e.g., prophylactic and therapeutic agents for infectious diseases drugs for animals, drugs for fishes, pesticides, and food preservatives. For use as a medicament or drugs for animals, the derivative may be optionally added a pharmaceutical acceptable carrier and prepared into pharmaceutical compositions of various dosage forms such as parenteral (e.g., injection, transrectal, ophthalmic and oral dosage forms.

Examples of preparation for injection include aseptic or non-aqueous forms, suspensions, and emulsions, which are pharmaceutically acceptable. Examples of appropriate non-aqueous carriers, diluents, solvents, and vehicles include propylene glycol, polyethylene glycol, vegetable oil (e.g., olive oil), and injectable organic esters (e.g., ethyl oleate). Such pharmaceutical compositions may further contain adjuvants such as an antiseptic agent, a humectant, an emulsifying agent, and a dispersant. These compositions may be sterilized through filtration by means of a bacterial filter, or through addition of a sterilizer immediately before use. Alternatively, a sterilized solid composition containing a sterilizing agent, which can be dissolved in a small mount of sterilized injection medium, may be used.

Preferably, ophthalmic agents containing the compound of the present invention may contain a solubilizing agent, a preservative, an isotonic agent, or a thickener.

Examples of solid agents for oral administration include capsules, tablets, pills, powder, and granules. The solid agents are generally prepared through mixing the compound of the present invention with at least one inert diluent such as sucrose, lactose, or starch. During routine preparation of the solid agents, in addition to the inert diluent, an additional substance such as a lubricant (e.g., magnesium stearate) may be employed. In the case of capsules, tablets, and pills, a buffer may further be employed. Tablets and pills may be coated with enteric coating.

Examples of liquid agents for oral administration include pharmaceutically acceptable emulsions, solutions, suspensions, syrups, and elixirs, which contain an inert diluent generally employed in the art, such as water. In addition to the inert diluent, the compositions may further contain an adjuvant such as a humectant, an emulsifying agent, a suspending agent, a sweetener, and a flavoring agent.

Preferably, transrectal agents containing the compound of the present invention may contain vehicles such as cacao fat and suppository wax.

The dose of the pyridonecarboxylic acid derivative (1) of the present invention or a salt thereof, which varies depending on properties of the compound, the route of administration, the desired period of treatment, or other factors, is generally about 0.1 to 1,000 mg/kg/day, particularly preferably about 0.5 to 100 mg/kg/day. If desired, the daily dose may be divided into 2 to 4 portions.

EXAMPLES

The present invention will be described in more detail by way of Examples and Referential Examples hereafter, which should not be construed as limiting the invention thereto.

Referential Example 1

Synthesis of 1-diphenylmethyl-3-mesyloxyazetidine

Triethylamine (153 mL) was added to a methylene chloride solution (1 L) of 1-diphenylmethyl-3-hydroxyazetidine (239 g) at room temperature, and methanesulfonyl chloride (85 mL) was added dropwise to the mixture under cooling with ice. The mixture was returned to room temperature, and stirred for two hours. The reaction mixture was washed with water (1 L), and the organic layer was dried with sodium sulfate anhydrate, followed by removal of solvent under reduced pressure. The precipitated solid was dispersed in hexane and collected through filtration, to thereby yield 313 g of the title compound.

Form: Colorless solid
m.p.: 115-116° C.
$^1$H-NMR (CDCl$_3$) δ:
2.98 (s, 3H), 3.20 (m, 2H), 3.64 (m, 2H), 4.40 (s, 1H), 5.10 (m, 1H), 7.20 (t, J=7 Hz, 2H), 7.28 (dd, J=7 Hz, 7 Hz, 4H), 7.39 (d, J=7 Hz, 4H)

Referential Example 2

Synthesis of N-isopropylazetidin-3-ylamine Dihydrochloride

1-Diphenylmethyl-3-mesyloxyazetidine (47.6 g) and isopropylamine (59.1 g) was dissolved in ethanol (800 mL), and the mixture was stirred at 50° C. for 42 hours. The solvent was removed under reduced pressure, and the residue was extracted with ethyl acetate (500 mL). The extract was washed with a 1% aqueous sodium carbonate solution (500 mL), and the organic layer was dried and concentrated under reduced pressure. The residue was subjected to column chromatography (silica gel, dichloromethane/ethyl acetate=4/1→dichloromethane/methanol=10/1), to thereby yield a colorless solid (33.5 g). The solid was dissolved in dichloromethane (100 mL), and 14% hydrochloric acid/dioxane (70 mL) was added to the solution under cooling with ice. After addition of the entirety, diethyl ether (500 mL) was added to the mixture, followed by thoroughly stirring. The formed solid was collected through filtration and washed with diisopropyl ether (100 mL). The washed solid was dissolved in methanol (500 mL), and the solvent was removed under reduced pressure. The residue was dissolved in methanol (200 mL), and the solution was subjected to hydrogenation in the presence of Pd(OH)$_2$/C (1.45 g) at 40° C. for 17 hours. The catalyst was filtered out, and the filtrate was concentrated under reduced pressure. Diisopropyl ether (200 mL) was added to the residue, and the precipitate was collected through filtration, to thereby yield (20.6 g) of the title compound.

Form: Colorless solid m.p. 144-1470

$^1$H-NMR (d$_6$-DMSO) δ:

1.21 (s, 6H), 3.25-3.34 (m, 1H) 409-4.19 (m, 2H), 4.21-4.30 (m, 1H), 4.31-4.39 (m, 2H), 9.00-10.6 (brs, 4H)

Referential Example 3

N-tert-butylazetidin-3-ylamine dihydrochloride

In a manner similar to that of Referential Example 2, the title compound was obtained Form: Yellow oil $^1$H-NMR (CDCl$_3$) δ:

1.27 (s, 9H) 4.06-4.20 (m, 2H), 4.29-4.37 (m, 1H), 4.38-4.46 (m, 2H), 9.15-956 (brs, 1H) 9.59-10.00 (brs, 1H), 10.20-10.60 (brs, 2H)

Referential Example 4

Synthesis of ethyl 8-bromo-1-[6-(tert-butylamino)-3,5-difluoropyridin-2-yl]-6,7-difluoro-4-oxo-1,4-dihydroquinolin-3-carboxylate To a chloroform solution (5 mL) of ethyl 3-ethoxy-2-(3-bromo-2,4,5-trifluorobenzoyl)acrylate (1.32 g), which had been produced through a conventional method from ethyl 3-bromo-2,4,5-trifluorobenzoylacetate, 2-amino-6-(tert-butylamino)-3,5-difluoropyridine was added until conversion to the aminoacrylate form was complete, while the progress of reaction was monitored though TLC. The solution was concentrated under reduced pressure, to thereby obtain a yellow solid residue. Potassium carbonate anhydrate (1.2 g) and N,N-dimethylformamide (2 mL) were added to the residue, and the mixture was stirred at 90° C. for 15 minutes. The mixture was left to cool, and chloroform (30 mL) and distilled water (300 mL) were added, and separated Subsequently, the chloroform layer was washed twice with distilled water (300 mL) and dried over magnesium sulfate anhydrate. The dried product was concentrated under reduced pressure and left to stand. The precipitation was collected through filtration, washed sequentially with ethanol and diisopropyl ether, to thereby yield the 1.41 g of the title compound as a colorless powder.

m.p.: 198-203° C.

$^1$H-NMR (CDCl$_3$) δ:

1.38 (s, 9H), 1.40 (t, J=7 Hz, 3H), 4.04 (q, J=7 Hz, 2H) 4.71 (brs, H), 7.20 (dd, J=8 Hz, 1 Hz, 1H), 8.36 (dd, J=9 Hz, 10 Hz, 1H), 8.54 (s, 1H)

Referential Example 5

In a manner similar to that of Referential Example 4, the following compounds (1) to (10) were produced.

(1) Ethyl 1-[6-(tert-butylamino)-3,5-difluoropyridin-2-yl]-8-chloro-6,7-difluoro-4-oxo-1,4-dihydroquinolin-3-carboxylate m.p.: 203-205° C.

$^1$H-NMR (d$_6$-DMSO) δ:

1.39 (s, 9H), 1.40 (t, J=7 Hz, 3H), 4.40 (q, J=7 Hz, 2H) 4.70 (brs, 1H), 7.21 (dd, J=8 Hz, 1 Hz, 1H), 8.31 (dd, J=8 Hz, 10 Hz, 1H), 8.50 (s, 1H)

(2) Ethyl 1-[6-(tert-butylamino)-3,5-difluoropyridin-2-yl]-6,7-difluoro-8-methyl-4-oxo-1,4-dihydroquinolin-3-carboxylate m.p.: 207-211° C.

$^1$H-NMR (d$_6$-DMSO) δ:

1.34-1.48 (m, 12H), 1.82 (d, J=3 Hz, 3H), 4.40 (q, J=7 Hz, 2H) 4.75 (brs, 1H), 7.23 (t, J=9 Hz, 1H), 8.22 (t, J=10 Hz, 1H), 8.50 (s, 1H)

(3) Ethyl 8-chloro-1-(3,5-difluoro-6-isopropylaminopyridin-2-yl)-6,7-difluoro-4-oxo-1,4-dihydroquinolin-3-carboxylate m.p.: 206-209° C.

$^1$H-NMR (CDCl$_3$) δ;

1.20 (d, J=7 Hz, 3H), 1.24 (d, J=7 Hz, 3H), 1.40 (t, J=7 Hz, 3H), 4.11 (m, 1H), 4.40 (q, J=7 Hz, 2H), 4.60 (brs, 1H), 7.22 (dd, J=8 Hz, 9 Hz, 1H), 8.32 (dd, J=8 Hz, 10 Hz, 1H), 8.49 (s, 1H)

(4) Ethyl 1-(6-amino-5-chloro-3-fluoropyridin-2-yl)-8-chloro-6,7-difluoro-4-oxo-1,4-dihydroquinolin-3-carboxylate m.p. 186-189° C.

$^1$H-NMR (CDCl$_3$) δ;

1.40 (t, J=7 Hz, 3H), 4.40 (q, J=7 Hz, 2H), 5.02 (brs, 2H), 7.57 (d, J=8 Hz, 1H), 8.30 (t, J=9 Hz, 1H), 8.48 (s, 1H)

(5) Ethyl 1-(6-amino-5-fluoro-3-methylpyridin-2-yl)-8-chloro-6,7-difluoro-4-oxo-1,4-dihydroquinolin-3-carboxylate m.p.: 198-202° C.

$^1$H-NMR (CDCl$_3$) δ;

1.40 (t, J=7 Hz, 3H), 2.02 (s, 3H), 4.39 (q J=7 Hz, 2H), 4.7 (brs, 2H), 7.25 (d, J=10 Hz, 1H), 8.34 (t, J=10 Hz, 1H), 8.34 (s, 1H)

(6) Ethyl 1-[6-(tert-butylamino-3-chloro-5-fluoropyridin-2-yl]-8-chloro-6,7-difluoro-4-oxo-1,4-dihydroquinolin-3-carboxylate m.p.: 210-213° C.

$^1$H-NMR (CDCl$_3$) δ;

1.38 (s, 9H), 1.41 (t, J=7 Hz, 3H), 4.41 (q, J=7 Hz, 2H), 4.84 (brs, 1H), 7.32 (d, J=10 Hz, 1H), 8.32 (dd, J=8 Hz, 10 Hz, 1H), 8.45 (s, 1H)

(7) Ethyl 8-chloro-1-(3,5-difluoro-6-methylaminopyridin-2-yl)-6,7-difluoro-4-oxo-1,4-dihydroquinolin-3-carboxylate m.p.: 207-209° C.

$^1$H-NMR (CDCl$_3$) δ;

1.41 (t, J=7 Hz, 3H), 2.98 (d, J=5 Hz, 3H), 4.41 (q, J=7 Hz, 2H), 4.85 (brs, 1H), 7.23 (dd, J=8 Hz, 9 Hz, 1H), 8.32 (dd, J=8 Hz, 10 Hz, 1H), 8.48 (s, 1H)

(8) Ethyl 8-bromo-1-(3,5-difluoro-6-methylaminopyridin-2-yl)-6,7-difluoro-4-oxo-1,4-dihydroquinolin-3-carboxylate
$^1$H-NMR (d$_6$-DMSO) δ:
1.26 (t, J=7 Hz, 3H), 2.74 (d, J=4 Hz, 3H), 4.23 (q, J=7 Hz, 2H), 7.17-7.23 (m, 1H), 7.94 (dd, J=8 Hz, 10 Hz, H), 7.96 (dd, J=10 Hz, 10 Hz, 1H), 8.62 (s, 1H)
(9) Ethyl 1-(3,5-difluoro-6-methylaminopyridin-2-yl)-6,7-difluoro-8-methyl-4-oxo-1,4-dihydroquinolin-3-carboxylate
$^1$H-NMR (d$_6$-DMSO) δ:
1.26 (t, J=7 Hz, 3H), 1.76 (d, J=3 Hz, 3H), 2.77 (d, J=5 Hz, 3H), 4.22 (q, J=7 Hz, 2H), 7.26-7.31 (m, 1H), 7.95 (dd, J=9 Hz, 10 Hz, 1H), 8.05 (dd, J=10 Hz, 10 Hz, 1H), 8.56 (s, 1H)
(10) Ethyl 1-(6-ethylamino-3,5-difluoropyridin-2-yl)-6,7-difluoro-8-methyl-4-oxo-1,4-dihydroquinolin-3-carboxylate
$^1$H-NMR (d$_6$-DMSO) δ:
1.09 (t, J=7 Hz, 3H), 0.25 (t, J=8 Hz, 3H), 0.77 (d, J=3 Hz, 3H), 3.21-3.29 (m, 2H), 4.22 (q, J=7 Hz, 2H), 7.27-7.32 (m, 1H), 7.95 (dd, J=9 Hz, 10 Hz, 1H), 8.05 (dd, J=10 Hz, 10 Hz, 1H), 8.56 (s, 1H)

Referential Example 6

Synthesis of 1-(6-amino-3,5-difluoropyridin-2-yl)-8-bromo-6,7-difluoro-4-oxo-1,4-dihydroquinolin-3-carboxylic acid Ethyl 8-bromo-1-[6-(tert-butylamino)-3,5-difluoropyridin-2-yl]-6,7-difluoro-4-oxo-1,4-dihydroquinolin-3-carboxylate (1.38 g) was added to a liquid mixture of 14% hydrochloric acid (3.5 mL) and acetic acid (3.5 mL), followed by stirring for five hours under reflux. Distilled water (5 mL) was added to the mixture, and the mixture was left to cool. The precipitate was collected through filtration, and washed sequentially with ethanol and diisopropyl ether, to thereby yield 1.10 g of the title compound as a colorless powder.
m.p.: 272-278° C.
$^1$H-NMR (d$_6$-DMSO) δ:
6.80 (s, 2H), 7.99 (t, J=9 Hz, 1H), 8.38 (t, J=9 Hz, 1H), δ 93 (s, 1H)

Referential Example 7

In a manner similar to that of Referential Example 6, the following compounds (1) to (10) were produced.
(1) 1-(6-Amino-3,5-difluoropyridin-2-yl)-8-chloro-6,7-difluoro-4-oxo-1,4-dihydroquinolin-3-carboxylic acid
m.p.: ≧280° C.
$^1$H-NMR (d$_6$-DMSO) δ:
6.80 (s, 2H), 7.99 (t J=9 Hz, 1H), 8.38 (t, J=9 Hz, 1H), 8.93 (s, 1H)
(2) 1-(6-Amino-3,5-difluoropyridin-2-yl)-6,7-difluoro-8-methyl-4-oxo-1,4-dihydroquinolin-3-carboxylic acid
m.p.: 274-277° C.
$^1$H-NMR (d$_6$-DMSO) δ:
1.84 (s, 3H), 6.91 (brs, 2H), 8.03 (t, J=9 Hz, 1H), δ 25 (t, J=9 Hz, 1H), 8.93 (s, 1H)
(3) 8-Chloro-1-(3,5-difluoro-6-isopropylaminopyridin-2-yl)-6,7-difluoro-4-oxo-1,4-dihydroquinolin-3-carboxylic acid
m.p.: 226-230° C.
$^1$H-NMR (d$_6$-DMSO) δ;
1.10 (d, J=7 Hz, 3H), 1.16 (d, J=7 Hz, 3H), 3.94 (m, 1H) 7.02 (brd, J=8 Hz, 1H), 7.97 (t, J=9 Hz, 1H), 8.39 (t, J=9 Hz, 1H), 8.92 (s, 1H)
(4) 1-(6-Amino-5-chloro-3-fluoropyridin-2-yl)-8-chloro-6,7-difluoro-4-oxo-1,4-dihydroquinolin-3-carboxylic acid
m.p.: ≧280° C.
$^1$H-NMR (d$_6$-DMSO) δ;
6.86 (brs/2H), 8.15 (d, J=9 Hz, 1H), 8.38 (t, J=9 Hz, 1H), 8.95 (s, 1H)
(5) 1-(6-Amino-5-fluoro-3-methylpyridin-2-yl)-8-chloro-6,7-difluoro-4-oxo-1,4-dihydroquinolin-3-carboxylic acid
m.p.: 279-284° C. (decomposition)
$^1$H-NMR (d$_6$-DMSO) δ;
1.94 (s, 3H), 6.62 (brs, 2H), 7.57 (d, J=11 Hz, 1H), 8.40 (t, J=9 Hz, 1H), 8.72 (s, 1H)
(6) 1-(6-Amino-3-chloro-5-fluoropyridin-2-yl)-8-chloro-6,7-difluoro-4-oxo-1,4-dihydroquinolin-3-carboxylic acid
m.p.: ≧280° C.
$^1$H-NMR (d$_6$-DMSO) δ;
7.10 (brs, 2H), 7.99 (d, J=10 Hz, 1H), 8.40 (t, J=10 Hz, 1H), 8.89 (s, 1H)
(7) 8-Chloro-1-(3,5-difluoro-6-methylaminopyridin-2-yl)-6,7-difluoro-4-oxo-1,4-dihydroquinolin-3-carboxylic acid
m.p.: 236-242° C.
$^1$H-NMR (d$_6$-DMSO) δ;
2.76 (d, J=5 Hz, 3H), 7.21-7.28 (m 1H), 7.98 (dd, J=9 Hz, 10 Hz, 1H), 8.39 (dd, J=9 Hz, 10 Hz, 1H), 8.92 (s, 1H)
(8) 8-Bromo-1-(3,5-difluoro-6-methylaminopyridin-2-yl)-6,7-difluoro-4-oxo-1,4-dihydroquinolin-3-carboxylic acid
$^1$H-NMR (d$_6$-DMSO) δ:
2.75 (d, J=5 Hz, 3H), 7.19-7.28 (m, 1H), 7.96 (dd, J=9 Hz, 10 Hz, 1H), 8.40 (dd, J=9 Hz, 10 Hz, 1H), 8.90 (s, 1H)
(9) 1-(3,5-Difluoro-6-methylaminopyridin-2-yl)-6,7-difluoro-8-methyl-4-oxo-1,4-dihydroquinolin-3-carboxylic acid
$^1$H-NMR (d$_6$-DMSO) δ:
1.80-1.85 (d, J=2 Hz, 3H), 2.77 (d, J=5 Hz, 3H), 7.29-7.38 (m, 1H), 7.97 (dd, J=9 Hz, 10 Hz, 1H), 8.22 (dd, J=9 Hz, 9 Hz, 1H), 8.89 (s, 1H)
(10) 1-(6-Ethylamino-3,5-difluoropyridin-2-yl)-6,7-difluoro-8-methyl-4-oxo-1,4-dihydroquinolin-3-carboxylic acid
$^1$H-NMR (d$_6$-DMSO) δ:
1.09 (t, J=6 Hz, 3H), 1.83 (d, J=2 Hz, 3H), 3.21-3.30 (m, 2H), 7.32-7.39 (m, 1H), 7.97 (dd, J=9 Hz, 10 Hz, 1H), 8.23 (dd, J=9 Hz, 9 Hz, 1H), 8.89 (s, 1H)

Example 1

Synthesis of 1-(6-Amino-3,5-difluoropyridin-2-yl)-8-bromo-6-fluoro-7-(3-isopropylaminoazetidin-1-yl)-4-oxo-1,4-dihydroquinolin-3-carboxylic acid (compound 1)

N-isopropylazetidin-3-ylamine dihydrochloride (374 mg), 1-(6-amino-3,5-difluoropyridin-2-yl)-8-bromo-6,7-difluoro-4-oxo-1,4-dihydroquinolin-3-carboxylic acid (518 mg), N-methylpyrrolidine (0.8 mL), lithium chloride (500 mg) and dimethyl sulfoxide (1.5 mL) were mixed, and the mixture was stirred at 50° C. for 4.5 hours. After the mixture had been left to cool, diethyl ether (10 mL) was added to the mixture and stirred, followed by removing the supernatant. The same procedure was repeated three times. Water (3 mL) was added to the residue, and the pH of the mixture was adjusted to 6 by use of aqueous citric acid solution. The formed solid was collected through filtration, washed three times with water (3 mL), then suspended in ethanol (10 mL), and stirred under heating. The formed solid was collected through filtration, and suspended in diisopropyl ether (10 mL), followed by stirring under heating. The heated suspension was filtrated to yield 410 mg of the title compound.
Form: Pale yellow powder
m.p.: ≧203° C., decomposition
$^1$H-NMR (d$_6$-DMSO) δ:
0.94 (d, J=6 Hz, 6H), 2.68-2.75 (m, 1H) 3.60-3.67 (m, 1H), 4.02-4.11 (m, 2H), 4.65-4.73 (m, 2H), 6.74 (s, 2H), 7.88 (d, J=4 Hz, 1H), 7.93 (dd, J=10 Hz, 10 Hz, H), 8.69 (s, 1H)

Example 2

In a manner similar to that of Example 1, the following compounds 2 to 11 were synthesized.

(1) 1-(6-Amino-3,5-difluoropyridin-2-yl)-8-chloro-6-fluoro-7-(3-isopropylaminoazetidin-1-yl)-4-oxo-1,4-dihydroquinolin-3-carboxylic acid (compound 2)
Form: Pale yellow powder
m.p: ≧205° C., decomposition
$^1$H-NMR (d$_6$-DMSO) δ:
1.17 (d, J=6 Hz, 6H), 3.13-3.24 (m, 1H), 3.98-4.15 (m, 1H), 4.44-4.58 (m, 2H), 4.72-4.83 (m, 2H), 6.75 (s, 2H), 7.93 (d, J=14 Hz, 1H), 7.95 (dd, J=10 Hz, 1 Hz, 1H), 8.72 (s, 1H)

(2) 1-(6-Amino-3,5-difluoropyridin-2-yl)-6-fluoro-7-(3-isopropylaminoazetidin-1-yl)-8-ethyl-4-oxo-1,4-dihydroquinolin-3-carboxylic acid (compound 3)
Form: Pale yellow powder
m.p.: ≧238° C. decomposition
$^1$H-NMR (d$_6$-DMSO) δ:
0.93 (d, J=7 Hz, 6H), 1.62 (s, 3H), 2.66-2.75 (m, 1H), 3.60-3.69 (m, 1H), 3.76-3.86 (m, 1H), 4.39-4.54 (m, 2H), 6.82 (s, 2H), 7.74 (d, J=14 Hz, 1H), 7.94 (dd, J=10 Hz, 10 Hz, 1H), 8.69 (s, 1H)

(3) 1-(6-Amino-3,5-difluoropyridin-2-yl)-8-bromo-7-(3-tert-butylaminoazetidin-1-yl)-6-fluoro-4-oxo-1,4-dihydroquinolin-3-carboxylic acid (compound 4)
Form: Pale yellow powder
m.p.: ≧225° C., decomposition
$^1$H-NMR (D$_6$-DMSO) δ:
0.99 (s, 9H), 3.72-3.81 (m, 1H), 3.97-4.10 (m, 2H), 4.68-4.78 (m, 2H), 6.74 (s, 2H), 7.88 (d, J=14 Hz, 1H), 7.93 (dd, J=10 Hz, 10 Hz, 1H), 8.70 (s, 1H)

(4) 1-(6-Amino-3,5-difluoropyridin-2-yl)-7-(3-tert-butylaminoazetidin-1-yl)-8-chloro-6-fluoro-4-oxo-1,4-dihydroquinolin-3-carboxylic acid (compound 5)
Form: Pale yellow powder
m.p.: ≧250° C., decomposition
$^1$H-NM (d$_6$-DMSO) δ:
1.00 (s, 9H), 3.75-3.85 (m, 1H), 4.03-4.18 (m, 2H), 4.68-4.77 (m, 2H), 6.74 (s, 2H), 7.87 (d, J=14 Hz, 1H), 7.94 (dd, J=10 Hz, 10 Hz, 1H), 8.68 (s, 1H)

(5) 1-(6-Amino-3,5-difluoropyridin-2-yl)-7-(3-tert-butylaminoazetidin-1-yl)-6-fluoro-8-methyl-4-oxo-1,4-dihydroquinolin-3-carboxylic acid (compound 6)
Form: Pale yellow powder
m.p.: ≧193° C., decomposition
$^1$H-NMR (d$_6$-DMSO) δ:
1.08 (s, 9H), 1.65 (s, 3H), 3.87-4.02 (m, 2H), 4.06-4.18 (m, 1H), 4.49-4.62 (m, 2H), 6.84 (s, 2H), 7.80 (d, J=14 Hz, 1H), 7.96 (dd, J=10 Hz, 10 Hz, 1H), 8.72 (s, 1H)

(6) 1-(3,5-Difluoro-6-methylaminopyridin-2-yl)-6-fluoro-7-(3-isopropylaminoazetidin-1-yl)-8-methyl-4-oxo-1,4-dihydroquinolin-3-carboxylic acid (compound 7)
Form: Colorless powder
m.p.: ≧218° C., decomposition
$^1$H-NMR (d$_6$-DMSO) δ:
0.93 (d, J=6 Hz, 6H), 0.62 (s, 3H), 2.80 (d, j=4 Hz, 3H), 3.61-3.71 (m, 1H), 3.79-3.88 (m, 1H), 3.89-3.97 (m, 1H), 4.41-4.53 (m, 2H), 7.24-7.28 (m, 1H), 7.77 (d, J=14 Hz, 1H), 7.95 (dd, J=10 Hz, 10 Hz, 1H), 8.71 (s, 1H)

(7) 1-(6-Ethylamino-3,5-difluoropyridin-2-yl)-6-fluoro-7-(3-isopropylaminoazetidin-1-yl)-8-methyl-4-oxo-1,4-dihydroquinolin-3-carboxylic acid (compound 8)
Form: Pale yellow powder
m.p.: ≧202° C., decomposition
$^1$H-NMR (d$_6$-DMSO) δ:
0.94 (d, j=6 Hz, 6H), 1.14 (t, J=7 Hz, 3H), 1.63 (s, 3H), 3.62-3.73 (m, 1H), 3.83-3.97 (m, 1H), 4.41-4.53 (m, 2H), 7.24-7.29 (m, 1H), 7.77 (d, J=14 Hz, 1H), 7.95 (dd, J=10 Hz, 10 Hz, 1H), 8.70 (s, 1H)

(8) 8-Chloro-1-(3,5-difluoro-6-methylaminopyridin-2-yl)-6-fluoro-7-(3-isopropylaminoazetidin-1-yl)-4-oxo-1,4-dihydroquinolin-3-carboxylic acid (compound 9)
Form: Colorless Powder
m.p.: ≧244° C., decomposition
$^1$H-NMR (D$_6$-DMSO) δ:
1.15 (brs, 6H), 2.77 (d, J=4 Hz, 3H), 3.99-4.14 (m, 1H), 4.36-4.57 (m, 2H), 4.71-4.82 (m, 2H), 7.16-7.25 (m, 1H), 7.91-7.98 (m, 2H), 8.73 (s, 1H)

(9) 8-Chloro-1-(3,5-difluoro-6-isopropylaminopyridin-2-yl)-6-fluoro-7-(3-isopropylaminoazetidin-1-yl)-4-oxo-1,4-dihydroquinolin-3-carboxylic acid (compound 10)
Form: Colorless powder
m.p.: ≧248° C., decomposition
$^1$H-NMR (d$_6$-DMSO) δ:
1.11-1.22 (m, 12H), 3.92-4.00 (m, 1H), 4.09-4.18 (m, 1H), 4.36-4.53 (m, 2H), 4.63-4.77 (m, 2H), 6.89 (d, J=8 Hz, 1H), 7.81 (d, J=13 Hz, 1H), 7.91 (dd, J=10 Hz, 10 Hz, 1H), 8.44 (s, 1H)

(10) 8-Bromo-1-(3,5-difluoro-6-methylaminopyridin-2-yl)-6-fluoro-7-(3-isopropylaminoazetidin-1-yl)-4-oxo-1,4-dihydroquinolin-3-carboxylic acid (compound 11)
Form: Pale yellow powder
m.p.: ≧220° C., decomposition
$^1$H-NMR (d$_6$-DMSO) δ:
1.15 (brs, 6H), 2.77 (d, J=5 Hz, 3H), 3.96-4.17 (m, 1H), 4.32-4.55 (m, 2H), 4.70-4.84 (m, 2H), 7.15-7.24 (m, 1H), 7.90-8.00 (m, 2H), 8.75 (s, 1H)

Example 3

Synthesis of 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid maleic acid salt (compound 12)

1-(6-Amino-3,5-difluoropyridin-2-yl)-8-bromo-6-fluoro-7-(3-isopropylaminoazetidin-1-yl)-4-oxo-1,4-dihydroquinolin-3-carboxylic acid (132 mg) and maleic acid (58 mg) were added to ethanol (3 mL), and the mixture was heated at 80° C. Water was gradually added to the mixture until the compounds were completely dissolved. After the solution had been left to cool, the formed solid was collected through filtration, to thereby yield 102 mg of the title compound.
Form: Pale yellow powder
m.p.: ≧220° C., decomposition
$^1$H-NMR (d$_6$-DMSO) δ:
1.9 (d, J=7 Hz, 6H), 4.13-4.22 (m, 1H3, 4.42-4.59 (m, 2H), 4.71-4.86 (m, 2H), 6.02 (s, 2H), 6.75 (s, 2H), 7.93 (dd, J=10 Hz, 10 Hz, H), 7.96 (d, J=14 Hz, 1H3, 8.75 (s, 1H3, 8.58-9.51 (brs, 1H)

Example 4

In a manner similar to that of Example 3, the following compounds 13 to 19 were produced.

(1) 1-(6-Amino-3,5-difluoropyridin-2-yl)-8-bromo-6-fluoro-7-(3-isopropylaminoazetidin-1-yl)-4-oxo-1,4-dihydroquinolin-3-carboxylic acid methanesulfonic acid salt (compound 13)
Form: Pale yellow powder
m.p.: ≧224° C., decomposition
$^1$H-NMR (d$_6$-DMSO) δ:
1.24 (d, J=7 Hz, 6H), 2.30 (s, 3H), 4.14-4.24 (m, 1H), 4.44-4.62 (m, 2H), 4.73-4.86 (m, 2H), 6.75 (s, 2H), 7.94 (dd, J=10 Hz, 10 Hz, 1H), 7.96 (d, J=14 Hz, 1H), 8.75 (s, 1H), 8.96-9.35 (brs, 0.5H)

(2) 1-(6-Amino-3,5-difluoropyridin-2-yl)-8-bromo-6-fluoro-7-(3-isopropylaminoazetidin-yl)-4-oxo-1,4-dihydroquinolin-3-carboxylic acid p-toluenesulfonic acid salt (compound 14)
Form: Pale yellow powder
m.p.: ≧235° C., decomposition
$^1$H-NMR (d$_6$-DMSO) δ:
1.21 (d, J=6 Hz, 6H), 2.28 (s, 3H), 4.15-4.26 (m, 1H), 4.43-4.62 (m, 2H), 4.70-4.87 (m, 2H), 6.75 (s, 2H), 7.09 (d, J=8 Hz, 2H), 7.47 (d, J=9 Hz, 2H), 7.94 (dd, J=10 Hz, 10 Hz, 1H), 7.96 (d, J=14 Hz, 1H), 8.75 (s, 1H), 8.93-9.11 (brs, 1H)

(3) 1-(6-Amino-3,5-difluoropyridin-2-yl)-8-bromo-6-fluoro-7-(3-isopropylaminoazetidin-1-yl)-4-oxo-1,4-dihydroquinolin-3-carboxylic acid hydrochloride (compound 15)
Form: Pale yellow powder
m.p.: ≧210° C., decomposition
$^1$H-NMR (d$_6$-DMSO) δ:
1.21 (d, J=5 Hz, 6H), 4.11-4.22 (m, 1H), 4.49-4.65 (m, 2H), 4.73-4.86 (m, 2H), 6.75 (s, 2H), 7.94 (dd, J=10 Hz, 10 Hz, 1H), 7.97 (d, J=14 Hz, 1H), 8.74 (s, 1H), 9.32-9.81 (brs, 2H)

(4) 1-(6-Amino-3,5-d-fluoropyridin-2-yl)-6-fluoro-7-(3-isopropylaminoazetidin-1-yl)-8-methyl-4-oxo-1,4-dihydroquinolin-3-carboxylic acid methanesulfonic acid salt (compound 16)
Form: Pale yellow powder
m.p.: ≧235° C., decomposition
$^1$H-NMR (d$_6$-DMSO) δ:
121 (d, J=7 Hz, 6H), 1.68 (s, 3H), 2.31 (s, 3H), 3.41□3.47 (m, 1H), 4.17-4.50 (m, 2H), 4.51-4.70 (m, 2H), 6.85 (s, 2H), 7.84 (d, J=12 Hz, 1H), 7.96 (dd, J=10 Hz, 1 Hz, 1H), 8.75 (s, 1H), 9.00 (brs, 2H)

(5) 1-(6-Amino-3,5-difluoropyridin-2-yl)-6-fluoro-7-(3-isopropylaminoazetidin-1-yl)-8-methyl-4-oxo-1,4-dihydroquinolin-3-carboxylic acid p-toluenesulfonic acid salt (compound 17)
Form: Yellow powder
m.p.: ≧232° C., decomposition
$^1$H-NMR (d$_6$-DMSO) δ:
1.21 (d, J=6 Hz, 6H), 1.67 (s, 3H), 2.28 (s, 3H), 3.41□3.47 (m, 1H), 4.15-4.30 (m, 2H), 4.37-4.47 (m, 1H), 4.50-4.69 (m, 2H), 6.86 (s, 2H), 7.10 (d, J=8 Hz, 2H), 7.47 (d, J=8 Hz, 2H), 7.84 (d, J=14 Hz, 1H), 7.96 (dd, J=10 Hz, 1 Hz, 1H), 8.76 (s, 1H), 8.98 (brs, 2H)

(6) 1-(6-Amino-3,5-difluoropyridin-2-yl)-6-fluoro-7-(3-isopropylaminoazetidin-1-yl)-8-methyl-4-oxo-1,4-dihydroquinolin-3-carboxylic acid maleic acid salt (compound 18)
Form: Pale yellow powder
m.p.: ≧235° C., decomposition
$^1$H-NMR (d$_6$-DMSO) δ:
1.20 (d, J=6 Hz, 6H), 1.68 (s, 3H), 4.15-4.28 (m, 2H), 4.33-4.44 (m, 1H), 4.50-4.68 (m, 2H), 6.03 (s, 2H), 6.86 (s, 2H), 7.84 (d, J=14 Hz, 1H), 7.96 (dd, J=10 Hz, 10 Hz, 1H), 8.76 (s, 1H (7) 1-(6-Amino-3,5-difluoropyridin-2-yl)-6-fluoro-7-(3-isopropylaminoazetidin-1-yl)-8-methyl-4-oxo-1,4-dihydroquinolin-3-carboxylic acid hydrochloride (compound 19)
Form: Colorless powder
m.p.: ≧230° C., decomposition
$^1$H-NMR (d$_6$-DMSO) δ:
1.22 (d, J=6 Hz, 6H), 1.68 (s, 3H), 3.41-3.47 (m, 1H), 4.15-4.40 (m 2H), 4.42-4.67 (m, 2H), 6.86 (s, 2H), 7.84 (d, J=14 Hz, 1H), 7.96 (dd, J=10 Hz, 10 Hz, 1H), 8.75 (s, 1H), 9.45 (brs, 1.5H)

The compounds in the present invention were tested for their antibacterial activity, phototoxicity, binding rate to serum proteins, and pharmacokinetics. The results on these tests are given in Text Example 1 to 4. As comparative compounds, the following compounds as disclosed in International Publication Nos. 97/111068 and 01/02390 were employed.

Comparative compound 1: 1-(6-amino-3,5-difluoropyridin-2-yl)-8-bromo-6-fluoro-7-(3-methylaminoazetidin-1-yl)-4-oxo-1,4-dihydroquinolin-3-carboxylic acid Comparative compound 2: 1-(6-amino-3,5-difluoropyridin-2-yl) 8-bromo-7-(3-ethylaminoazetidin-1-yl)-6-fluoro-4-oxo-1,4-dihydroquinolin-3-carboxylic acid Comparative compound 3: 1-(6-amino-3,5-difluoropyridin-2-yl) 8-bromo-6-fluoro-7-(3-methylaminoazetidin-1-yl)-4-oxo-1,4-dihydroquinolin-3-carboxylic acid maleic acid salt Comparative compound 4: 1-(6-amino-3,5-difluoropyridin-2-yl) 8-bromo-7-(3-ethylaminoazetidin-1-yl)-6-fluoro-4-oxo-1,4-dihydroquinolin-3-carboxylic acid maleic acid salt Test Example 1

Antibacterial Activity

Minimum inhibitory concentration (MIC: μg/mL) of the compounds shown in Table 1 was determined according to the standard method of the Japanese Society of Chemotherapy (CHEMOTHERAPY 29(1), 76, 1981). The results are shown in Table 1

TABLE 1

|  | compound 1 | Comp. compound 1 | Comp. compound 2 |
| --- | --- | --- | --- |
| *M. luteus* IFO12708 | 0.12 | 0.25 | 0.25 |
| MRSA W44 | 0.03 | 0.06 | 0.06 |
| *S. haemolytlcus* 67 | 4 | 8 | 8 |
| *P. mirabilis* IFO3849 | 0.25 | 0.5 | 0.25 |

MIC value: (μg/mL)

Test Example 2

Phototoxicity

The compounds shown in table 2 were subjected to the below-described phototoxicity test.

Each test compound was intravenously administered (40 mg/10 mL/kg) to female ICR mice (5- to 6-weeks old), and the mice were irradiated with UV-rays (320 to 400 nm, 1.8 mW/cm$^2$/sec) for four hours. Abnormalities induced in the ear of each mouse were observed immediately after (0 hour), 24 hours after, and 48 hours after the irradiation. The abnormality was evaluated according to the following criteria: normal (0 point), slight erythema (score 1), medium erythema (score 2), and serious erythema or edema (score 3). The results are shown in Table 2.

TABLE 2

| Compound | 0 hour (Score, incidence) | 24 hours | 48 hours |
|---|---|---|---|
| compound 1 | 0, 0/3 | 0, 0/3 | 0, 0/3 |
| Comp. compound 1 | 0, 0/3 | 0, 0/3 | 0, 0/3 |
| Comp. compound 2 | 0, 0/3 | 0, 0/3 | 0, 0/3 |

Test Example 3

Binding Rate to Proteins

Binding rate to proteins of the compounds shown in Table 3 was determined by ultrafiltration method. Specifically, a 0.5 mg/mL DMSO solution of each compound was diluted with human serum or a 0.4% phosphate buffer (pH: 7.4 containing 0.5% NaCl) to thereby prepare a 5 µg/mL solution. The human serum solution was incubated at 37° C. for 30 minutes and centrifugally filtrated through a filter (pore size: 0.22 µm). A portion of the serum filtrate and the phosphate buffer solution were applied to an HPLC system, and the peak area of the compound was measured. Binding rate of each compound to human serum proteins was calculated by the following equation 1:

Binding rate (%)=$(A-B) \times 100/A$ (equation 1)

A: Peak area (in phosphate buffer)
B: Peak area (in serum filtrate)

TABLE 3

| | Binding rate to proteins (%) |
|---|---|
| Comp. compound 1 | 49.0 |
| Comp. compound 2 | 62.8 |
| compound 1 | 64.0 |
| compound 3 | 44.3 |
| compound 4 | 44.9 |
| compound 6 | 26.8 |
| compound 12 | 64.0 |

These results revealed that the compounds in the present invention showed low binding rate to proteins without exhibiting the increase in binding rate as anticipated from the increase in its lipophilicity.

Test Example 4

Pharmacokinetics

Absorbability of the compounds shown in Table 4 was investigated in dogs. Specifically, a 0.5% methylcellulose suspension of each test compound (10 mg/kg) was forcedly orally administered to 2- to 4-years old male beagle dogs which had been fasted for 16 to 17 hours. The blood was collected from each dog at 0.25, 0.5, 1, 2, 4, 6, 8, and 24 hours after the administration, and the serum level of the test compound was determined to evaluate absorbability of the compound. The results are shown in Table 4.

TABLE 4

| Example No. | n | $C_{max}$ (µg/mL) | $T_{max}$ (h) | $T_{1/2}$ (h) | AUC0 to 8 h (µg·h/mL) |
|---|---|---|---|---|---|
| compound 12 | 3 | 5.25 | 1 | 5.8 | 30.9 |
| Comp. compound 3 | 3 | 1.49 | 1 | 3.2 | 7.6 |
| Comp. compound 4 | 3 | 3.73 | 1 | 4.3 | 17.5 |

As shown in Table 4, pharmacokinetics of compound 12 in the present invention is remarkably improved as compared with comparative compounds 3 and 4.

The invention claimed is:

1. A pyridonecarboxylic acid derivative represented by formula (1):

(1)

or a salt thereof, wherein $R^1$ represents a methyl group, a fluorine atom, or a chlorine atom; $R^2$ represents a hydrogen atom or a lower alkyl group; $R^3$ represents an isopropyl group or a tert-butyl group; $R^4$ represents a methyl group or a halogen atom; and $R^5$ represents a fluorine atom or a chlorine atom.

2. The pyridonecarboxylic acid derivative or the salt thereof according to claim 1, wherein $R^1$ and $R^5$ each are a fluorine atom.

3. The pyridonecarboxylic acid derivative or the salt thereof according to claim 1, wherein $R^4$ a bromine atom or a methyl group.

4. The pyridonecarboxylic acid derivative or the salt thereof according to claim 1, wherein $R^2$ is a hydrogen atom or a methyl group.

5. 1-(6-Amino-3,5-difluoropyridin-2-yl)-6-fluoro-7-(3-isopropylaminoazetidin-1-yl)-8-methyl-4-oxo-1,4-dihydroquinolin-3-carboxylic acid or a salt thereof.

6. A medicament comprising the pyridonecarboxylic acid derivative or the salt thereof according to any one of claims 1 to 5 as an active ingredient.

7. An antibacterial agent comprising the pyridonecarboxylic acid derivative or the salt thereof according to any one of claims 1 to 5 as an active ingredient.

8. A pharmaceutical composition comprising the pyridonecarboxylic acid derivative or the salt thereof according to any one of claims 1 to 5, and a pharmaceutically acceptable carrier.

9. A pyridonecarboxylic acid derivative represented by formula (2):

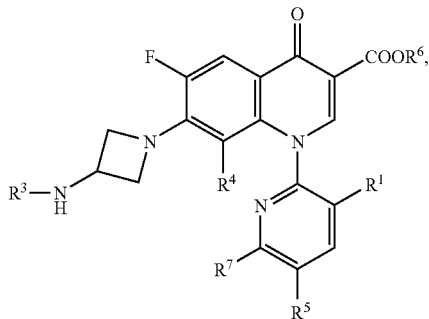

or a salt thereof, wherein $R^1$ represents a methyl group, a fluorine atom, or a chlorine atom; $R^3$ represents an isopropyl group or a tert-butyl group; $R^4$ represents a methyl group or a halogen atom; $R^5$ represents a fluorine atom or a chlorine atom; $R^6$ represents a hydrogen atom or a carboxyl protective group; and $R^7$ represents —$NR^2R^8$, wherein $R^2$ represents a hydrogen atom or a lower alkyl group, and $R^8$ represents a hydrogen atom or an amino protective group, with the proviso that $R^6$ and $R^8$ do not simultaneously represent hydrogen atoms.

10. The pyridonecarboxylic acid derivative or the salt thereof according to claim 2, wherein $R^4$ is a bromine atom or a methyl group.

11. The pyridonecarboxylic acid derivative or the salt thereof according to claim 2, wherein $R^2$ is a hydrogen atom or a methyl group.

12. The pyridonecarboxylic acid derivative or the salt thereof according to claim 3, wherein $R^2$ is a hydrogen atom or a methyl group.

13. The pyridonecarboxylic acid derivative or salt thereof according to claim 1, wherein $R^1$ is a fluorine atom, $R^2$ a hydrogen atom, $R^4$ a bromine atom and $R^5$ is a fluorine atom.

14. The pyridonecarboxylic acid derivative or salt thereof according to claim 1, selected from the group consisting of 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid, 1-(6-amino-3,5-difluoropyridin-2-yl)-8-chloro-6-fluoro-7-(3-isopropylaminoazetidin-1-yl)-4-oxo-1,4-dihydroquinolin-3-carboxylic acid, 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid, 1-(6-amino-3,5-difluoropyridin-2-yl)-8-bromo-7-(3-tert-butylaminoazetidin-1-yl)-6-fluoro-4-oxo-1,4-dihydroquinolin-3-carboxylic acid, 1-(6-amino-3,5-difluoropyridin-2-yl)-7-(3-tert-butylaminoazetidin-1-yl)-8-chloro-6-fluoro-4-oxo-1,4-dihydroquinolin-3-carboxylic acid, 1-(6-amino-3,5-difluoropyridin-2-yl)-7-(3-tert-butylaminoazetidin-1-yl)-6-fluoro-8-methyl-4-oxo-1,4-dihydroquinolin-3-carboxylic acid, 1-(3,5-difluoro-6-methylaminopyridin-2-yl)-6-fluoro-7-(3-isopropylaminoazetidin-1-yl)-8-methyl-4-oxo-1,4-dihydroquinolin-3-carboxylic acid, 1-(6-ethylamino-3,5-difluoropyridin-2-yl)-6-fluoro-7-(3-isopropylaminoazetidin-1-yl)-8-methyl-4-oxo-1,4-dihydroquinolin-3-carboxylic acid, 8-chloro-1-(3,5-difluoro-6-methylaminopyridin-2-yl)-6-fluoro-7-(3-isopropylaminoazetidin-1-yl)-4-oxo-1,4-dihydroquinolin-3-carboxylic acid, 8-chloro-1-(3,5-difluoro-6-isopropylaminopyridin-2-yl)-6-fluoro-7-(3-isopropylaminoazetidin-1-yl)-4-oxo-1,4-dihydroquinolin-3-carboxylic acid, 8-bromo-1-(3,5-difluoro-6-methylaminopyridin-2-yl)-6-fluoro-7-(3-isopropylaminoazetidin-1-yl)-4-oxo-1,4-dihydroquinolin-3-carboxylic acid, 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid maleic acid salt, 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid methanesulfonic acid salt, 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid p-toluenesulfonic acid salt, 1-(6-amino-3,5-difluoropyridin-2-yl)-8-bromo-6-fluoro-7-(3-isopropylaminoazetidin-1-yl)-4-oxo-1,4-dihydroquinolin-3-carboxylic acid hydrochloride, 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid methanesulfonic acid salt, 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid p-toluenesulfonic acid salt, 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid maleic acid salt, and 1-(6-amino-3,5-difluoropyridin-2-yl)-6-fluoro-7-(3-isopropylaminoazetidin-1-yl)-8-methyl-4-oxo-1,4-dihydroquinolin-3-carboxylic acid hydrochloride.

15. A method for treating at least one of a bacterial infection and a microbial infection, comprising:
administering the pyridonecarboxylic acid derivative or the salt thereof according to claim 1 to a mammal suffering from at least one of the bacterial infection and the microbial infection.

16. The method of claim 15, wherein the mammal is a human.

* * * * *